United States Patent [19]

Sussman

[11] Patent Number: 4,578,057
[45] Date of Patent: Mar. 25, 1986

[54] VENTRICULAR RIGHT ANGLE CONNECTOR AND SYSTEM

[75] Inventor: Marvin L. Sussman, Miami, Fla.

[73] Assignee: Cordis Corporation, Miami, Fla.

[21] Appl. No.: 645,849

[22] Filed: Aug. 31, 1984

[51] Int. Cl.[4] ............................................. A61F 2/20
[52] U.S. Cl. ....................................... 604/9; 604/167
[58] Field of Search ................................. 604/8–10, 604/164–171, 175, 117, 268, 905, 83

[56] References Cited

U.S. PATENT DOCUMENTS

| | | | |
|---|---|---|---|
| 3,444,861 | 5/1969 | Schulte | 604/9 |
| 3,459,188 | 9/1969 | Roberts | 604/164 |
| 3,595,240 | 6/1971 | Mishler | 604/9 |
| 3,915,168 | 10/1975 | Monestere, Jr. et al. | 604/164 |
| 4,000,739 | 1/1977 | Stevens | 604/167 |
| 4,014,333 | 3/1977 | McIntyre | 604/167 |
| 4,430,081 | 2/1984 | Timmermans | 604/167 |
| 4,475,898 | 10/1984 | Brodner et al. | 604/9 |

OTHER PUBLICATIONS

Hakim, Soloman, "The Cordis-Hakim Valve System for Ventricular Shunting", 1/83, p. 2.

Primary Examiner—C. Fred Rosenbaum
Assistant Examiner—Karen L. Kaechele
Attorney, Agent, or Firm—Lockwood, Alex, Fitzgibbon & Cummings

[57] ABSTRACT

A ventricular hydrocephalus treatment system is provided which includes a right angle connector having a self-sealing port that is in general alignment with a distal end opening of the right angle connector in order to provide for implanting passage of a stylet through the self-sealing port and into a ventricular catheter projecting through the proximal end opening. The ventricular catheter is an integral part of a tubing assembly that also includes a hydrocephalus valve for regulating the flow of cerebrospinal fluid through the ventricular catheter after implantation into a ventricle of the brain.

9 Claims, 4 Drawing Figures

U.S. Patent    Mar. 25, 1986    4,578,057
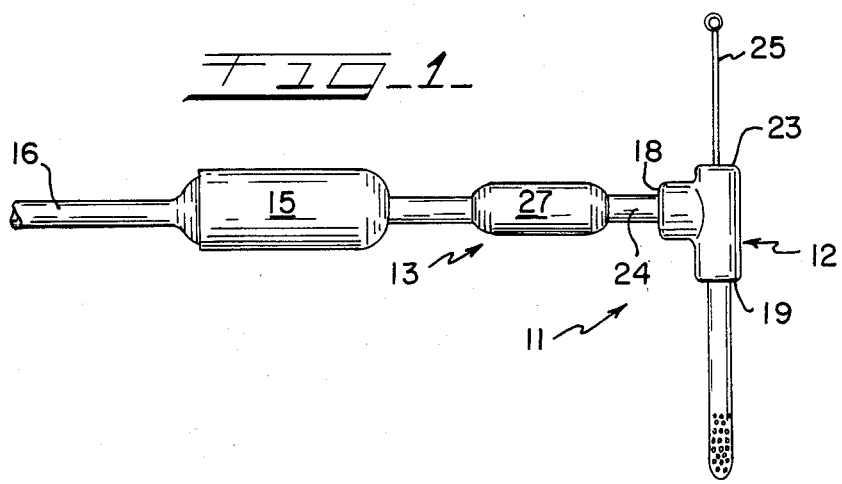
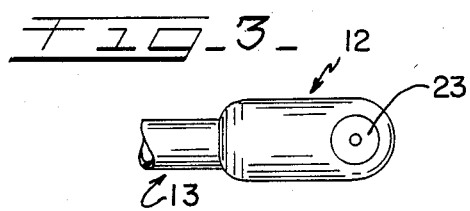
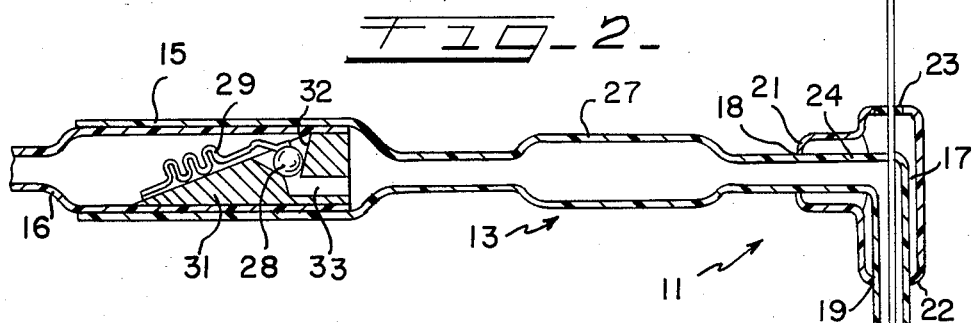
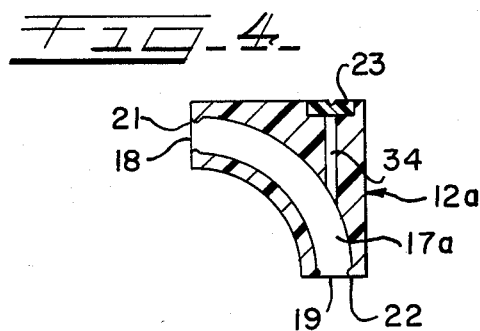

VENTRICULAR RIGHT ANGLE CONNECTOR AND SYSTEM

This invention generally relates to devices for the drainage of cerebrospinal fluid from the ventricle of the brain, and more particularly to structures for improving the ease and reliability of implantation. An important aspect of this invention is the inclusion of a right angle connector that is generally elbow-shaped and that has a passageway therethrough that is large enough for passing a ventricular catheter therethrough and that includes a self-sealing port that is in generally straight-line alignment with a distal end outlet thereof through which the ventricular catheter passes. In another aspect of this invention, the right angle connector is part of a system that also includes a length of tubing passing therethrough, which tubing has a ventricular catheter at its distal end and includes a cerebrospinal fluid drainage valve mounted therealong and caudad the right angle connector.

Hydrocephalus is a condition characterized by an abnormal increase in the amount of cerebrospinal fluid within the brain cavity, which is usually accompanied by an enlargement of the head and which typically leads to brain damage. Hydrocephalus has been treated for a number of years by surgical procedures which include implanting a valve or shunt in the skull. Such valves or shunts typically include a ventricular catheter having drainage ports that open into a ventricle of the brain, the ventricular catheter having a lumen therethrough that allows cerebrospinal fluid to flow from its drainage ports, through a tube, and through a one-way cerebrospinal fluid drainage valve mounted therealong. These assemblies provide controlled drainage of cerebrospinal fluid out of the brain ventricle to thereby relieve the buildup of cerebrospinal fluid pressure that leads to hydrocephalus or similar conditions.

In many applications of these hydrocephalus catheter and drainage valve assemblies, the fluid is intended to drain into the atrium of the heart or into the peritoneal cavity of the patient, which typically requires bending of the catheter tubing through approximately 90° in order to change the orientation of the tubing from that projecting out of the ventricle to that generally parallel to the skull. In as much as ventricular catheter tubing material is soft and pliable, this generally right angular directional change would often result in kinking of the catheter tubing or possible damage thereto as it traverses the bone of the skull. Accordingly, generally rigid right angle connectors have been provided to connect, usually in conjunction with suture tying, the ventricular catheter to the drainage tubing.

More particularly, current systems in this regard typically include a right angle connector, one end of which is positioned within the burr hole drilled in the cranial vault or skull through which the ventricular catheter has been implanted. This end of the right angle connector is suture-tied to the catheter after the excess length of the ventricular catheter is trimmed off and the trimmed end is slipped over the distal end of the right angle conenctor. Often the catheter is tied to the right angle connector with a suture at a location below the outer surface of the burr hole. The tubing including the cerebrospinal fluid drainage valve is similarly slipped over and suture-tied to the proximal end of the right angle connector. Typically, these right angle connectors are fabricated from a stainless steel tube which has been bent to form a right angle. These devices require a substantial amount of effort in order to properly align, cut and size the components after catheter implantation and also to suture the components together after implantation. This activity, especially suture tying within the burr hole, creates situations in which the ventricular catheter may be inadvertently dislodged from its implanted position, while also requiring addition time for completing the implantation procedure.

There is accordingly a need for a system and right angle connector thereof which minimizes the amount of manipulation that is needed in order to implant a ventricular catheter and mount same in connection with a right angle connector. There is an associated need for a ventricular catheter and hydrocephalus valve system that can be implanted in a relatively short period of time and that does not require substantial assembly during implantation, which assembly can lead to unintentional dislodgement of the ventricular catheter from its desired location within the brain ventricle.

The present invention meets these needs by providing a right angle connector for this type of ventricular catheter and hydrocephalus valve implantation, which right angle connector includes a passageway therethrough, which passageway has a distal end opening and a proximal end opening, the passageway being large enough to pass a ventricular catheter therethrough. A tubing unit having a ventricular catheter at its distal end and a cerebrospinal fluid drainage valve mounted caudad thereof is inserted through the proximal end opening and then the distal end opening of the passageway through the right angle connector. A self-sealing port is provided through a wall of the right angle connector at a location in generally straight-lined alignment with the distal end opening of the passageway, which self-sealing port permits a stylet to be inserted therethrough and to the distal tip of a ventricular catheter in order to implant same. After implantation, the stylet is removed, the port seals itself, and cerebrospinal fluid can begin to drain through the catheter and tubing to the extent that it passes through the hydrocephalus valve.

It is accordingly a general object of the present invention to provide an improved right angle connector and ventricular catheter and valve system including same.

Another object of the present invention is to provide an improved hydrocephalus valve system that utilizes a right angle connector having a self-sealing port through which a stylet can be passed in order to properly implant the ventricular catheter.

Another object of the present invention is to provide an improved right angle connector for a hydrocephalus treatment unit which requires no suture tying assembly of the ventricular catheter to the valve portion of the unit.

These and other objects of the present invention will be apparent from the following description of this invention, taken in conjunction with the accompanying drawings, wherein:

FIG. 1 is a perspective view of the assembly system according to this invention, including the right angle connector and the tubing assembly including a ventricular catheter and a hydrocephalus valve;

FIG. 2 is a longitudinal cross-section through the assembly system of FIG. 1;

FIG. 3 is a top plan view of the assembly system illustrated FIG. 1; and

FIG. 4 is a longitudinal sectional view through an alternative embodiment of the right angle connector.

A hydrocephalus treatment system, which is generally designated by reference numeral 11 in FIGS. 1, 2 and 3, includes a right angle connector, generally designated as 12, and a tubing assembly or unit, generally designated as 13. Tubing unit 13 includes a distal portion or ventricular catheter 14, a hydrocephalus valve 15, and a caudal tubing portion 16. When the system 11 is implanted, the ventricular catheter 14 opens into a ventricle of the brain, from which fluid is drained through the tubing unit 13, including its hydrocephalus valve 15 and its caudal tubing portion 16. Typically, the caudal tubing portion 16 will be appropriately connected to tubing (not shown) for drainage into the atrium of the heart or into the peritoneal cavity of the patient.

With more particular reference to the right angle connector 12, such is a generally elbow-shaped tubular member having an internal passageway 17, which has a proximal end opening 18 and a distal end opening 19. Internal passageway 17 is sized to permit passage of the ventricular catheter 14 therethrough. Each end opening 18, 19 includes an O-ring or lip 21, 22 for sealingly engaging the tubing unit 13 as generally shown in order to prevent leakage out of the right angle connector 12 of any cerebrospinal fluid that may seep thereinto. Right angle connector 12 also includes a self-sealing port 23 that is of generally known construction. The self-sealing port 23 is in generally straight-line alignment with the distal end opening 19 of the internal passageway 17.

When the distal portion or ventricular catheter 14 of the tubing unit 13 has been fed through the internal passageway 17 of the implanted right angle connector 12 to the extent illustrated in the drawings, which is until a portion 24 of the tubing unit 13 that is cephalad of the hydrocephalus valve 15 is within the internal passageway 17, a stylet 25 punctures the self-sealing port 23 and a location along the cephalad portion 24 of the tubing unit 13, after which the stylet 25 is passed through the ventricular catheter 14 to its distal tip in order to appropriately implant the ventricular catheter 14 within a ventricle of the brain. Excess cerebrospinal fluid passes from the ventricle through orifices 26. After the catheter is thus implanted and once the caudal tubing portion 16 is appropriately directed to the selected drainage location, for example by connecting additional tubing thereto and by implanting the additional tubing as necessary and conventional, the hydrocephalus treatment system 11 is ready for use.

Usually, the self-sealing port 23 will be made of a known material for such structures, such as Silastic rubber under compression. The remainder of the right angle connector 12 may be made of any suitable material that is biocompatible. Typically same may be molded out of a biocompatible polymeric material that is generally rigid, such as polypropylene, polyethersulfone, or the like. Materials other than polymers could be suitable, but they would be more difficult to fabricate to provide the desired shape, the lips 21 and 22, and the self-sealing port 23.

The tubing unit 13 is preferably provided as a single unit assembly of the ventricular catheter 14, the hydrocephalus valve 15, the caudal tubing portion 16, the tubing portion 24 that is a cephalad of the hydrocephalus valve 15, and an optional but preferred antechamber or pumping chamber 27 along the cephalic tubing portion 24. Except for certain internal components of the valve 15 and perhaps of the antechamber 27, the tubing unit is made of a flexible biocompatible material such as a silicone elastomer or a silicone elastomer impregnated with barium sulfate or the like.

The antechamber 27, which is of generally known construction and positioning, includes walls made of a resilient and deformable material, which may be compressed to restrict or stop the flow of fluid through the antechamber 27 in order to locate and clear clogged areas, or to test for clogging. Antechamber 27 may also be utilized to receive a small hypodermic needle probe for taking pressure readings or fluid samples.

Hydrocephalus valve 15 can be one of various constructions, including the valve that is illustrated in the drawings, which is generally in accordance with U.S. Pat. Nos. 3,288,142 and 3,527,226, the subject matter thereof being incorporated by reference hereinto. A valve of this type includes a ball or sphere 28, typically a synthetic sapphire, and a spring 29, typically of stainless steel, both of which are mounted on a valve body 31, preferably also made of stainless steel. Valve body 31 includes a conically shaped bore 32 of a passageway 33 through the valve body 31 and thus through the hydrocephalus valve 15. The resistance provided by the valve spring 29 determines the cerebrospinal fluid pressure at which the cerebrospinal fluid within the brain ventricle and the ventricular catheter 14 will move the sphere 28 from its seated position within the conically shaped bore 32 in order to thereby control the flow of cerebrospinal fluid through the tubing unit 13.

FIG. 4 illustrates an alternative right angle connector 12a that functions in substantially the same manner as connector 12. This connector 12a includes an internal passageway 17a that lies along a generally arcuate axis and that has an internal cross-sectional shape that is substantially the same as the shape of the generally medial portion 24 (typically circular) and that has a cross-sectional size or perimeter that is only somewhat larger than the outside perimeter of the cephalic tubing portion 24. Such internal passageway 17a is large enough to allow passage of the venticular catheter 14 and cephalic tubing portion 24 therethrough while providing close, secure and curved support for the cephalic tubing portion 24 in order to minimize the chance of kinking thereof or damage thereto as a result of its bending at this location. If necessary, depending upon the spacing between the self-sealing port 23 and the internal passageway 17a, a stylet-receiving lumen 34 may be included as shown.

It is to be appreciated that this invention can be embodied in various forms and therefore is to be construed and limited only by the scope of the appended claims.

I claim:

1. A right angle connector, catheter and hydrocephalus valve system, comprising:

a tubing assembly having a ventricular catheter at its distal end, said tubing assembly including a cerebrospinal fluid drainage valve mounted therealong at a location caudal of said ventricular catheter, said tubing assembly also including a tubing portion that is cephalic of said cerebrospinal fluid drainage valve;

right angle connector means for insertingly receiving said ventricular catheter and at least a portion of said cephalic tubing portion, said right angle connector means being a substantially elbow-shaped tubular member having a passageway therethrough, said passageway having an internal cross-section that is greater than the external cross-section of the ventricular catheter and of the cephalic tubing portion, said passageway including a distal end opening and a proximal end opening, said right angle connector means and its said passageway being substantially closed and including means for substantially preventing leakage of cerebrospinal fluid from said right angle connector;

a self-sealing port is included on said right angle connector means, said self-sealing port being in generally straight-line alignment with said distal end opening of the passageway of the right angle connector means; and stylet means for puncturing passage through said self-sealing port, for puncturing passage through said cephalic tubing portion at a location that is caudal of said ventricular catheter and for inserting passage into said ventricular catheter, and said self-sealing port closes upon removal of said stylet means from the right angle connector for substantially preventing cerebrospinal fluid leakage therethrough and out of said right angle connector.

2. The right angle connector, catheter and hydrocephalus valve system according to claim 1, wherein said leakage preventing means includes a lip at said distal end opening and a lip at said proximal end opening, each said lip having an internal cross-section that is smaller than said internal cross-section of the passageway.

3. The right angle connector, catheter and hydrocephalus valve system according to claim 1, wherein said tubing assembly is a preassembled unit.

4. The right angle connector, catheter and hydrocephalus valve system according to claim 1, further including an antechamber between said cerebrospinal fluid drainage valve and said cephalic tubing portion.

5. The right angle connector, catheter and hydrocephalus valve system according to claim 1, wherein said passageway of the right angle connector means has a generally arcuate axis and a cross-sectional size that approximates but is larger than the cross-sectional external size of said cephalic tubing portion.

6. A right angle connector for receiving and for mounting a tubing assembly having a ventricular catheter at its distal end and a cerebrospinal fluid drainage valve mounted therealong at a location caudal of said ventricular catheter, the tubing assembly also including a tubing portion that is cephalic of said cerebrospinal fluid drainage valve, and said ventricular catheter receives stylet means wherein the right angle connector comprises:

a substantially elbow-shaped, generally tubular member having an internal passageway including a distal end opening and a proximal end opening, said internal passageway having an internal cross-section that is greater than the external cross-section of the ventricular catheter and of the cephalic tubing portion, said right angle connector and its internal passageway being substantially closed and including means for substantially preventing leakage of cerebrospinal fluid from said right angle connector;

a self-sealing port positioned between said internal passageway and an outside surface of the substantially elbow-shaped, generally tubular member;

said self-sealing port is in generally straight-line alignment with said distal end opening of the internal passageway; and said stylet means is for puncturing passage through said self-sealing port and for puncturing passage through said cephalic tubing portion at a location that is caudal of said ventricular catheter, and said self-sealing port closes upon removal of said stylet means from the right angle connector in order to substantially prevent leakage of cerebrospinal fluid therethrough.

7. The right angle connector according to claim 6, wherein said leakage preventing means includes a lip at said distal end opening and a lip at said proximal end opening, each said lip having an internal cross-section that is smaller than said internal cross-section of the passageway.

8. The right angle connector according to claim 6, wherein said internal passageway has a generally arcuate axis and a cross-sectional size that approximates but is larger than the external cross-section of the cephalic tubing portion such that the cephalic tubing portion contacts said internal passageway.

9. The right angle connector according to claim 6, wherein said internal passageway has a generally arcuate axis.

* * * * *